United States Patent [19]

Szantay et al.

[11] 4,044,012
[45] Aug. 23, 1977

[54] INDOLO-QUINOLIZIDINE DERIVATIVES

[75] Inventors: Csaba Szantay; Lajos Szabo; Gyorgy Kalaus; Egon Karpati; Laszlo Szporny, all of Budapest, Hungary

[73] Assignee: Richter Gedeon Vegyeszeti Gyar Rt., Budapest, Hungary

[21] Appl. No.: 670,243

[22] Filed: Mar. 25, 1976

Related U.S. Application Data

[62] Division of Ser. No. 575,038, May 6, 1975.

[30] Foreign Application Priority Data

May 7, 1974 Hungary .................. RI 536

[51] Int. Cl.² .................................. C07D 459/00
[52] U.S. Cl. .......................... 260/293.53; 424/267
[58] Field of Search ........................ 260/293.53

[56] References Cited

U.S. PATENT DOCUMENTS 3,925,392   12/1975   Najer et al. .................. 260/293.53

Primary Examiner—John D. Randolph
Attorney, Agent, or Firm—Toren, McGeady and Stanger

[57] ABSTRACT

New compounds of the formula

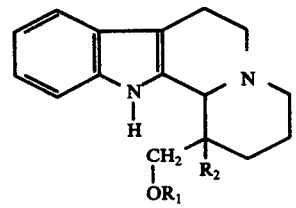

are provided wherein $R_1$ is hydrogen, and $R_2$ stands for an alkyl group and optically active enantiomers and pharmaceutically acceptable salts thereof.

2 Claims, No Drawings

INDOLO-QUINOLIZIDINE DERIVATIVES

This is a division of application Ser. No. 575,038, filed May 6, 1975.

This invention relates to new indolo-quinolizidine derivatives and pharmaceutical compositions containing the same, as well as to a process for the preparation thereof.

More particularly the invention relates to new indolo-quinolizidine derivatives having the general formula (I) or salts or optically active isomers of the same

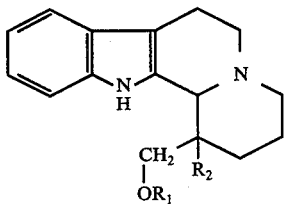

wherein
$R_1$ stands for hydrogen or an acyl group, and
$R_2$ stands for an alkyl group.

Those compounds of the general formula (I) wherein $R_1$ stands for hydrogen or an alkylcarbonyl group having optionally one or more substituents and $R_2$ stands for alkyl are particularly preferred.

The most preferred new compounds of the general formula (I) are those wherein $R_1$ stands for hydrogen, lower alkylcarbonyl, or benzoyl optionally having one or more alkoxy substituent(s).

The new compounds of the general formula (I) as well as the salts and optically active isomers thereof possess valuable pharmacological properties and can be used primarily as vasodilatating agents.

Several 1-disubstituted-indolo-quinolizidines have been described in the literature, some of which, such as vincamine and its derivatives, possess valuable pharmaceutical effects. The preparation of these disubstituted derivatives is described e.g. in J. Am. Chem. Soc. 87, 1580 (1965) and Tetrahedron Letters 1973, 191.

These known methods are, however, unsuitable to introduce a substituent into position 1 of the indoquinolizidine ring wherein the methylene group attached to the ring carbon atoms is connected to the remainder of the side chain through an oxygen atom.

The compounds of the general formula (I) or the salts or optically active isomers thereof are prepared according to the invention as follows: a compound of the general formula (II)

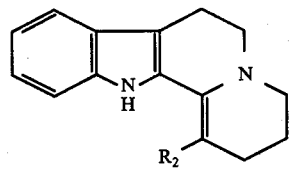

wherein $R_2$ stands for alkyl, is reacted with formaldehyde, and, if desired, the thus-obtained compound of the general formula (I), wherein $R_1$ stands for hydrogen and $R_2$ stands for alkyl, or a salt thereof is acylated, and, if desired, a compound of the general formula (I), wherein $R_1$ stands for acyl and $R_2$ stands for alkyl, is subjected to hydrolysis, and/or, if desired, a racemic compound of the general formula (I) or a salt thereof is resolved, and/or, if desired, a free base of the general formula (I) is converted into its salts, and/or, if desired, a salt of a compound of the general formula (I) is converted into the free base.

In the above formulae $R_2$ represents preferably a $C_{1-4}$ alkyl group, such as methyl, ethyl, propyl, isopropyl, butyl, isobutyl or tert.-butyl group.

The starting substances of the general formula (II) can be used either in the form of the free bases or as their salts, preferably as the acid addition salts formed e.g. with hydrochloric acid, hydrobromic acid, perchloric acid, perbromic acid, etc. When a salt of a compound having the general formula (II) is used as starting substance, this salt is converted into the free base prior to reacting it with formaldehyde. For this purpose preferably a base, e.g. a dilute aqueous solution of an inorganic base (such as an alkali hydroxide, e.g. sodium hydroxide, potassium hydroxide, etc.) can be used. The base can be used in a molar excess of about 20 to 40%. The free base of the general formula (II) is liberated from its salts preferably in an inert, water-immiscible organic solvent. As solvent e.g. a halogenated hydrocarbon, such as chloroform, carbon tetrachloride, dichloromethane, 1,2-dichloroethane, trichloroethylene, etc. can be used. The liberation of the base is performed preferably in an inert atmosphere, such as in nitrogen or argon atmosphere. Since the reaction proceeds in a two-phase mixture, it is preferable to apply constant stirring. The base liberates within a short time, generally after 5 to 20 minutes of stirring. The temperature of this reaction may vary within wide limits, the reaction is carried out, however, preferably at room temperature. When the reaction terminates the phases are separated from each other, the organic phase is dried, and subsequently concentrated to about 10 to 30% of its original volume. As drying agent preferably potassium carbonate is used, other well-known drying agents, however, can also be applied.

Thereafter the concentrate obtained in the above step is admixed with formaldehyde. Formaldehyde is introduced preferably in the form of paraformaldehyde. It is preferred to apply paraformaldehyde in a 1.5 to 3 molar excess related to the amount of the compound of the general formula (II). The reaction is performed at elevated temperatures, such as at 100° to 250° C, preferably at 160° to 170° C. Under such conditions the reaction proceeds generally within 3 to 5 hours, particularly within 4 hours.

In this reaction compounds of the general formula (I) containing a hydrogen atom as substituent $R_1$ are formed.

If a compound of the general formula (I) wherein $R_1$ stands for an acyl group is to be prepared, a compound of the general formula (I) wherein $R_1$ is hydrogen is treated with an appropriate acylating agent.

Any acylating agent known in the organic chemistry can be used in this reaction. The acylating agents suitable to acylate a hydroxy group attached to an aliphatic chain are particularly preferable.

As acylating agent e.g. an optionally substituted aliphatic, aromatic or heteroaromatic carboxylic acid or the respective acid halides or anhydrides, furthermore an optionally substituted aliphatic, aromatic or heteroaromatic sulfonic acid or the respective acid halides can be used. The primary aliphatic carboxylic anhydrides, such as acetic anhydride, propionic anhydride, etc., furthermore the optionally substituted aromatic carboxylic acids and the respective acid halides, such as benzoic acid, trimethoxybenzoyl chloride, etc., proved to be very advantageous acylating agents.

The acylation is carried out under well-known reaction conditions.

The necessary amount of the acylating agent depends on the reactivity of the starting substances, and may vary e.g. within 1 to 10 moles, such as within 1 to 5 moles calculated for 1 mole of the starting substance having the general formula (I). When a liquid acylating agent is used in great excess, this acylating agent may serve simultaneously as a solvent for the reaction.

If desired, a catalyst, such as iodine can be added to the reaction mixture in order to accelerate or complete, respectively, the acylation. When a free acid is used as acylating agent, preferably a dehydrating agent, such as dicyclohexyl carbodiimide is added to the reaction mixture. One may also add an acid binding agent, e.g. a tertiary organic base, such as pyridine, triethylamine, etc. to the mixture, particularly when an acid chloride or acid anhydride is used as acylating agent. The tertiary organic base can also be added in excess, in this event the base may serve simultaneously as a solvent for the reaction. It should be noted, however, that the use of catalysts, dehydrating agents or acid binding agents can be omitted when the components taking part in the acylation are sufficiently reactive per se.

The acylation is generally conducted in the presence of a solvent. As solvent, e.g. an excess of the acylating agent (such as propionic anhydride) or the tertiary organic base (such as pyridine) can be used, but inert organic solvents, such as dimethyl formamide, etc. can be applied as well.

The acylation is conducted under substantially anhydrous conditions. For this purpose dry chemicals, e.g. dry pyridine, dry dimethyl formamide, etc. should be used.

The temperature of the acylation may vary within wide limits depending on the nature of the starting substances and the solvent. The reaction temperature may range e.g. from 0° C up to the boiling point of the solvent, it is preferable, however, to conduct the reaction between room temperature and 100° C.

The reaction time also may vary within wide limits depending on the reaction temperature and on the nature of the starting substances. The reaction time may range e.g. from 10 minutes up to 6 days.

The reaction mixture obtained in the acylation step can be processed according to usual methods, e.g. by evaporating and alkalinating the reaction mixture, or by pouring the mixture onto ice, alkalinating the system, extracting the mixture and evaporating the extract, etc. When the reaction mixture is evaporated and the concentrate is rendered alkaline the base of the general formula (I), wherein $R_1$ stands for acyl group and $R_2$ stands for alkyl group, is generally obtained in well-filterable, crystalline state. If necessary, the obtained crystalline substance can be recrystallized easily from an appropriate solvent or solvent mixture. When the processing of the reaction mixture yields an oily substance, this oily substance can be crystallized generally very easily using conventional solvents, such as lower aliphatic alcohols, e.g. methanol.

If desired, the solid, powdery products can be purified by recrystallization from an appropriate solvent or solvent mixture. As solvents for recrystallization e.g. aliphatic alcohols, particularly lower aliphatic alcohols or their mixtures with water, such as methanol, aqueous methanol, etc. can be used.

The analysis data of the thus-obtained crystalline bases of the general formula (I) are in good agreement with the calculated values. The structures of the obtained products can be confirmed further by IR and NMR spectroscopy.

Those compounds of the general formula (I) wherein $R_1$ stands for acyl can be hydrolyzed to yield the corresponding compounds of the general formula (I) wherein $R_1$ is hydrogen. The hydrolysis is performed according to well-known methods, preferably using an acid or base as hydrolyzing agent.

The free bases of the general formula (I) can be converted into their acid addition salts. For this purpose preferably pharmaceutically acceptable mineral or organic acids, such as hydrogen halides (e.g. hydrochloric acid, hydrobromic acid), phosphoricacid, organic carboxylic acids (e.g. acetic acid, propionic acid, glycolic acid, maleic acid, succinic acid, tartaric acid, citric acid, salicylic acid or benzoic acid), alkylsulfonic acids (e.g. methanesulfonic acid), arylsulfonic acids (e.g. p-toluenesulfonic acid) etc. can be used. In turn, the acid addition salts can be treated with a base to yield the compounds of the general formula (I) in the form of the free bases.

The compounds of the general formula (I) contain an asymmetric carbon atom, thus they may exist in the form of optically active isomers. The synthesis according to the invention yields the end-products in racemic form, which can be resolved into the individual optically active isomers by well-known methods. The resolution can be performed after any step of the synthesis, thus, for example, one may resolve a compound of the general formula (I) wherein $R_1$ stands for hydrogen, and may use one of the thus-obtained optically active isomers in the subsequent acylation step.

As mentioned above the compounds of the general formula (I) and their pharmaceutically acceptable acid addition salts possess vasodilatating properties. The vasodilatating effects of the new compounds have been investigated by the following pharmacological experiments.

The tests were carried out on narcotized dogs. The results prove that the compounds possess significant vasodilatating effects. The compounds increase primarily the blood flow of the limbs, but some of them effectively increase the cerebral blood flow as well. In comparison with the significant increase of the blood flow, the temporary fall in blood pressure (lasting from about 1 to 2 minutes) and the increase of heart rate is relatively low.

The tests were performed on dogs narcotized with chloralose-urethane. The blood flow of the limbs was measured at the arteria femoralis, whereas the cerebral blood flow was investigated by measuring the flow of the arteria carotis interna. The circulation resistance was calculated from the blood pressure and blood flow walues.

The compounds under examination were dissolved in a pH 4 ascorbic acid solution, and vere administered in an intravenous dosage of 1 mg/kg. The observed changes were expressed as percentages in relation to the controls. 6 aminals were used in each of the individual tests. The data listed in Table 1 are the mean values calculated for the individual groups.

For comparison purposes the respective data of apovincaminic acid ethyl ester, the most active one of the compounds with related structures, are also listed in the Table.

Table 1

| Active agent | (1) | (2) | (3) | (4) | (5) | (6) |
|---|---|---|---|---|---|---|
| Apovincaminic acid ethyl ester | +58 | −35 | +16 | −20 | −28 | +14 |
| (A) | +183 | −59.5 | +36 | −37.5 | −17.5 | +16.5 |
| (B) | +237.5 | −74.5 | +2 | −13 | −39 | +13.5 |
| (C) | +234 | −74 | +113 | −63.5 | −36.5 | +58.5 |

Notes:
(1) blood flow of the limbs
(2) circulation resistance of the limb blood vessels
(3) cerebral blood flow
(4) circulation resistance of the cerebral blood vessels
(5) blood pressure
(6) heart rate
(A) a compound of the general formula (I) wherein $R_2$ is ethyl and $R_1$ is hydrogen
(B) a compound of the general formula (I) wherein $R_2$ is ethyl and $R_1$ is acetyl
(C) a compound of the general formula (I) wherein $R_2$ is ethyl and $R_1$ is propionyl As it appears from the data of the above Table the new compounds according to the invention are about four times as active as the reference substance with respect to the increase of the blood flow in the limbs, whereas their activities exceed more than three times that of the reference substance with respect to the increase of the cerebral blood flow.

The effective intravenous or oral dosage of the new compounds may vary within about 0.1 to 2 mg./kg. body weight. It should be noted, however, that the actual dosage is always determined in accordance with the needs of the patient, thus in some instances dosages lower or higher than those mentioned above are to be applied.

The compounds of the general formula (I) or the pharmaceutically acceptable acid addition salts thereof can be converted into pharmaceutical compositions suitable for enteral or parenteral administration. These compositions may contain the new compounds according to the invention either alone or in combination with other biologically active substances. When preparing the pharmaceutical compositions the active agent(s) is(are) admixed with conventional inert, non-toxic, pharmaceutically acceptable carriers and/or diluents. As carrier e.g. water, gelatine, lactose, starch, magnesium stearate, talc, vegetable oils, gum arabic, polyalkylene glycols, vaseline, etc. can be used. The compositions may optionally contain conventional pharmaceutical auxiliary agents, such as preservatives, salts for adjusting the osmotic pressure, buffers, flavouring agents, etc. The pharmaceutical compositions can be prepared in conventional forms, e.g. as solid formulations (tablets, coated tablets, capsules, etc.) or as liquid preparations (e.g. solutions, suspensions, emulsions, etc.) The obtained compositions can be sterilized or subjected to other finishing operations, if necessary.

The invention is elucidated in detail by the aid of the following non-limiting Examples.

EXAMPLE 1

1-Hydroxymethyl-1-ethyl-1,2,3,4,6,7,12,12b-octahydroindolo[2,3-a]quinolizine 10.0 g. (28.5 moles) of 1-ethyl-2,3,4,6,7,12-hexahydroindolo[2,3-a]quinolizine perchlorate are dissolved in 100 ml. of dichloromethane, and 75 ml. of distilled water and 20 ml. of a 2N sodium hydroxide solution are added to the dichloromethane solution in argon atmosphere under constant stirring. The reaction mixture is stirred for 10 minutes, thereafter the organic phase is separated, dried over anhydrous potassium carbonate, and filtered. The filtrate is concentrated in vacuo, under argon atmosphere, to a final volume of 15 ml., and 2.0 g. (66.8 mmoles) of paraformaldehyde are added to the concentrate. The solvent is evaporated in vacuo, and the residue is heated at 160°–170° C (bath temperature) for 4 hours in a closed vessel.

The obtained glassy substance is dissolved in hot methanol and the solution is allowed to cool, whereupon white crystals start to separate. The mixture is kept in refrigerator, thereafter the crystals are filtered off and washed with methanol. 4.15 g. of the title compound are obtained, m.p.: 232°–234° C. This substance is recrystallized from tenfold volume of methanol to yield 3.45 g. (42.7%) of the purified product: m.p.: 235°–236° C.

Analysis: Calculated for $C_{18}H_{24}N_2O$ (M = 284.39): C: 76.02%; H: 8.51%; N: 9.85%; Found: C: 76.16%; H: 8.61%; N: 10.18%.

IR-spectrum (in KBr-pellets): 3380 (ind-NH), 3140 – 2980 (—OH) cm$^{-1}$.

NMR-spectrum (DMSO-d$_6$) : τ = 0.7 (1H, ind =NH), 2.60–3.20 (4H, aromatic protons), 4.33 (1H, —OH), 6.52 (1H in the anellation position).

EXAMPLE 2

1-Acetoxymethyl-1-ethyl-1,2,3,4,6,7,12,12b-octahydroindolo[2,3-a]quinolizine 2.50 g. (8.82 mmoles) of 1-hydroxymethyl-1-ethyl-1,2,3,4,6,7,12,12b-octahydro-indolo[2,3-a]quinolizine are dissolved in 15 ml. of absolute pyridine. 15 ml. of acetic anhydride are added to the solution, and the mixture is allowed to stand at room temperature for three days. Thereafter the solution is evaporated in vacuo, and the oily residue is stirred with a 5% sodium hydrocarbonate solution. The separated solid substance is filtered off, washed with water, dried, and recrystallized first from aqueous methanol and then from methanol. 1.75 g. (61.2%) of the title compound are obtained in the form of shiny crystals melting at 96°–97° C.

Analysis: Calculated for $C_{20}H_{26}N_2O_2$ (M = 326.42): C: 73.59%; H: 8.03%; N:8.58%; Found: C: 73.59%; H: 8.06%; N: 8.66%.

IR-spectrum (in KBr pellet): 3370 (ind =NH), 1720 (=C=O) cm$^{-1}$.

NMR-spectrum (DMSO-d$_6$): τ = 1.38 (1H, indol =NH), 2.40 – 3.02 (4H, aromatic protons), 5.62 (2H, CH$_3$—CO—CH$_2$—), 6.51 (1H, in the anellation position), 7.76 (3H, CH$_3$—CO—).

EXAMPLE 3

1-Propionyloxymethyl-1-ethyl-1,2,3,4,6,7,12,12b-octahydro-indolo[2,3-a]quinolizine 0.50 g. of iodine are dissolved in 100 ml. of propionic anhydride, and 3.0 g. (10.5 mmoles) of 1-hydroxymethyl-1-ethyl-1,2,3,4,6,7,12,12b-octahydro-indolo[2,3-a]quinolizine are added in small portions to the red solution. The reaction mixture is immersed into a 50° C water bath for 15 minutes, then it is allowed to stand at room temperature for 16 hours.

The acidic solution is poured onto ice, the mixture is alkalinated with 40% sodium hydroxide solution (pH: 10 to 11), and extracted with 50 ml., 30 ml. and 20 ml. of dichloroethane. The organic extracts are combined, dried over magnesium sulfate, filtered, and the filtrate is evaporated in vacuo. The oily residue is crytallized from methanol. 2.10 g. (59.1%) of the title compound are obtained in the form of white crystals melting at 107°–108° C.

Analysis: Calculated for $C_{21}H_{28}N_2O_2$ (M = 340.45): C: 74.08%; H: 8.29%; N: 8.23%; Found: C: 74.14%; H: 8.44%; N: 8.12%.

IR-spectrum (in KBr-pellet): 3390 (ind. =NH), 1718 (=C=O) cm$^{-1}$.

EXAMPLE 4

1-Benzoyloxymethyl-1-ethyl-1,2,3,4,6,7,12,12b-octahydro-indolo[2,3-a]quinolizine 2.0 g. (7.02 mmoles) of .1-hydroxymethyl-1ethyl-1,2,3,4,6,7,12,12b-octahydro-indolo[2,3-a]quinolizine and 2.0 g. (16.4 mmoles) of benzoic acid are dissolved in 20 ml. of absolute dimethyl formamide, and a solution of 4.0 g. (19.5 mmoles) of dicyclohexyl carbodiimide in 15 ml. of absolute dimethyl formamide is added. The solution is allowed to stand at room temperature for two days, the separated solids are filtered off, and 1.0 g. (8.2 mmoles) of benzoic acid and 2.0 g. (9.7 mmoles) of dicyclohexyl carbodiimide are added to the filtrate. The filtrate is allowed to stand at room temperature for additional three days. The separated solids are filtered off, and the filtrate is evaporated in vacuo. The oily residue is stirred with a 5% sodium hydrocarbonate solution, the separated crystalline substance is filtered off, dried, and recrystallized first from aqueous methanol and then from methanol.

2.65 g. (97.1%) of the title compound are obtained as crystals melting at 148°–149° C.

Analysis: Calculated for $C_{22}H_{28}N_2O_2$ (M = 340.47): C: 77.29%; H: 7.27%; N: 7.21%; Found: C: 77.19%; H: 7.01%; N: 7.39%.

IR-spectrum (in KBr pellet): 3290 (ind.=NH), 1710 (=C=O) cm$^{-1}$.

EXAMPLE 5

1-(3,4,5-Trimethoxybenzoylmethyl)-1-ethyl-1,2,3,4,6,,7,12,12b-octahydro-indolo[2,3-a]quinolizine 1.30 g. (4.58 mmoles) of 1-hydroxymethyl-1-ethyl-1,2,3,4,6,7,12,12b-octahydro-indolo[2,3-a]quinolizine and 2.30 g. (10 mmoles) of 3,4,5-trimethoxybenzoyl chloride are dissolved in 15 ml. of absolute pyridine, and the solution is heated on a steam bath for 10 hours under a reflux condenser. The solution is evaporated in vacuo, and the oily residue is stirred first with a 5% sodium hydrocarbonate solution and then with distilled water. The separated solids are filtered off, dried, and recrystallized from methanol.

2.05 g. (93.5%) of the title compound are obtained as white crystals melting at 170°–171° C.

Analysis: Calculated for $C_{28}H_{34}N_2O_5$ (M = 478.57): C: 70.27%; H: 7.16%; N: 5.85%; Found: C: 70.08%; H: 7.09%; N: 5.61%.

IR-spectrum (in KBr pellet): 3381 (ind.=NH), 1698 (=C=O) cm$^{-1}$.

EXAMPLE 6

1-Hydroxymethyl-1-ethyl-1,2,3,4,6,7,12,12b-octahydro-indolo[2,3-a]quinolizine 1.50 g. (4.6 mmoles) of 1-acetoxymethyl-1-ethyl-1,2,3,4,6,7,12,12b-octahydro-indolo[2,3-a]quinolizine are dissolved in 15 ml. of methanol, and a solution of 0.40 g. (10 mmoles) of sodium hydroxide in 4 ml. of distilled water is added. The mixture is refluxed for 45 minutes, then diluted with 30 ml. of distilled water. The separated crystals are filtered off and washed with distilled water. 1.05 g. of the title compound are obtained; m.o.: 230°–233° C.

After recrystallization from methanol 0.95 g. (72.8%) of purified product are obtained; m.p.: 234°–236° C.

The analytical and spectral data of the obtained product are identical with those described in Example 1.

What we claim is:

1. A compound of the formula (I),

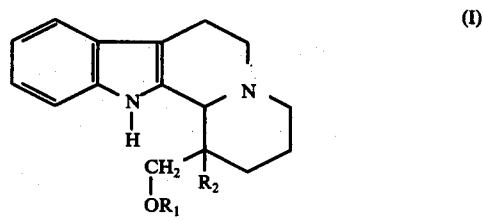

wherein $R_1$ stands for hydrogen, and $R_2$ stands for an alkyl group having 1 to 4 carbon atoms, the optically active enanthiomers and the pharmaceutically acceptable salts thereof.

2. 1-Hydroxymethyl-1-ethyl-1,2,3,4,6,7,12,12b-octahydro-indolo[2,3-a]quinolizine.

* * * * *